United States Patent [19]

Cipriani et al.

[11] 3,980,690

[45] Sept. 14, 1976

[54] PROCESS FOR THE CARBOXYLATION OF ALCOHOLS IN HETEROGENEOUS PHASE

[75] Inventors: Gioacchino Cipriani; Emilio Perrotti, both of San Donato Milanese, Italy

[73] Assignee: Snamprogetti S.p.A., San Donato Milanese, Italy

[22] Filed: July 25, 1974

[21] Appl. No.: 491,862

[30] Foreign Application Priority Data

Aug. 1, 1973 Italy .................................. 27388/73

[52] U.S. Cl. ................................................ 260/463
[51] Int. Cl.² ........................................... C07C 69/96
[58] Field of Search ...................................... 260/463

[56] References Cited
UNITED STATES PATENTS

| | | |
|---|---|---|
| 3,114,762 | 12/1963 | Mador et al. ........................ 260/463 |
| 3,227,740 | 1/1966 | Fenton ................................. 260/463 |
| 3,227,741 | 1/1966 | Fenton ................................. 260/463 |
| 3,445,497 | 5/1969 | Anderson et al. ............... 260/463 X |
| 3,625,995 | 12/1971 | Brattesani ....................... 260/463 X |
| 3,846,468 | 11/1974 | Perrotti et al. ...................... 260/463 |

*Primary Examiner*—Joseph P. Brust
*Attorney, Agent, or Firm*—Ralph M. Watson

[57] ABSTRACT

An alcohol is carboxylated into the corresponding carbonate by reacting the alcohol with oxygen and carbon dioxide in the presence of a catalyst system in the heterogeneous phase by introducing the reactants into a reactor charged with a catalyst, such as the complex system formed by copper and 4-vinylpyridine, causing the reactants to flow over the catalyst, and then withdrawing the products of the reaction and unconsumed reactants from the reactor.

4 Claims, No Drawings

PROCESS FOR THE CARBOXYLATION OF ALCOHOLS IN HETEROGENEOUS PHASE

The present invention relates to a process for the catalytic carboxylation of alcohols into the corresponding carbonates in the heterogeneous phase.

It is known from the Italian Patent Application No. 21468/A/70 filed on Mar. 4, 1940 in the name of the same Applicant (now Italian Pat. No. 890,077 ) and corresponding U.S. Pat. No. 3,846,468, that there is a process for obtaining carbonic acid esters, through reactions between the alcohol which is to be esterified, oxygen and carbon monoxide in the presence of a catalyst system constituted by transition metal complexes together with organic bases which are bound to the above-mentioned metals through coordinate bonds.

That process is carried out in solution and at the end of the reaction carbonate is separated by a fractional distillation from the employed solvent, which is, for the most part, the alcohol itself, and from the organic base.

It has been found that the carboxylation reaction may be carried out in the heterogeneous phase, the reactants being passed over the catalyst which, because of the continuous flow of material, does not undergo any alteration and can be regenerated.

According to the present invention the carboxylation reaction is carried out by feeding alcohol, carbon monoxide and oxygen to a catalyst system constituted by a complex formed by a metal and a polymer adapted to be bound thereto by a coordinate bond.

The polymeric matrix is generally selected from the polymers derived from nitrogenous bases containing unsaturated groups which can be caused to polymerize or copolymerize, such as vinylpyridines, vinylquinolines, vinylphenonthrolines, vinylimidazoles, or from polysulphoxides obtained by polymerizing olefines with $SO_2$, polyacrylonitrile and derivatives thereof, polydialkyldiamides. Moreover, among the polymeric bases, an advantageous use can be made of polymers having a matrix consisting of an inert carrier to which are bound, through chemical or hydrogen bonding, nitrogenous bases such as pyridine, o-phenanthroline, $\alpha,\alpha'$-dipyridyl, imidazole. Furthermore the polymers can be dispersed on inorganic solid carriers such as alumina, silica, silica-alumina and derivatives thereof.

The polymers thus formed, because of the presence of coordinating centers, are able to complex metal ions having two oxidation stages and able to easily pass from one another. In order to obtain the catalysts of the present invention use may be made of salts of metals belonging the the 1st B, 2nd and 8th groups of the periodic system. For instance, good use may be made of salts of metals selected among Cu, Ag, Au, Zn, Cd, Hg, Fe and Ni.

The most suitable anions, to which the metal ion is bound, are selected from halides, $CN^-$, $ClO_4^-$ or complex ions of the $BF_4^-$ type and the like.

The reaction goes on through an oxidation, by $O_2$, of the metal ion bound to the polymer to the highest oxidation state and a following reduction with CO. It can be carried out in two stages or in a continuous run; in the first case, a stream of oxygen and alcohol is first passed through the catalyst having the metal in the reduced state, so as to promote oxidation of the metal, then oxygen is replaced by carbon monoxide, carbonate being so obtained and the metal reverts to the reduced state. The process can, however, be easily and cheaply performed also as a continouous cycle, by sending a stream constituted by carbon monoxide, oxygen and alcohol on to the catalyst, and the mixture composition may be practically regulated with respect to carbon monoxide and oxygen so as to obtain the best production of carbonate.

The activity of the catalyst, after some cycles carried out both at separate feedings of CO and $O_2$, and at only one feeding, is practically unchanged.

In fact water, which is one of the reaction products and can deactivate the metal, does not accumulate since it is continuously removed from the catlyst because of the flow of the feed mixture. Moreover, under such conditions, there is the remarkable advantage due to the fact that the carbonate need not be separated from an organic base, since the organic base is constituted by the polymer itself which has a very low vapour pressure and moreover is insoluble in the products fed to the reaction phase.

The process can be carried out over a wide range of pressures and temperatures, and occurs also at atmospheric pressure and room temperature. Such factors can be changed in order to affect favorably the reaction kinetics and the limit values of the temperature depend only of the catalyst stability.

Pressure and temperature affect the physical state of the reactants and let the catalyst's behaviour remain unchanged so that the advantages of the heterogenoeus phase are maintained.

Generally the temperature ranges from 20° to 150°C, preferably from 50° to 80°C, while the pressure may range from the atmospheric one to 200 atmospheres without any modification and high reduction of the metals affecting the reaction referred to.

The reaction proceeds very well at atmospheric pressure. An increase thereof kinetically favours the process and such an influence remarkably occurs in the range of 1–30 atmospheres. The method followed in the preparation of the catalyst consists either in adding a solution of the optimum amount of the metal to the solution or dispersion of the polymer in alcohol or hydrocarbon solvents, or in forming a metal-monomer complex and then in polymerizing it. The following examples illustrate the invention without limiting it.

EXAMPLE 1

3.19 g of poly-4-vinylpyridine were dissolved into 60 cc of $CH_3OH$. Such a solution was added, drop by drop to a solution formed by 3.04 g. of CuCl in 100 cc of $CH_3CN$.

A light yellow precipitate was suddenly formed, very sensitive to air, which oxidized it into a green product. The product was obtained in quantitative yield and was analyzed as $Cu_1Cl_1$ (vinylpyridine($_{1,2}$ (it contained an excess of englobed vinylpyridine).

EXAMPLE 2

1.5 g. of catalyst were charged in a reactor under a pressure of 5 kg/cm². An $O_2$ flow, equal to 3000 cc/h, passed through a $CH_3OH$ trap at 50°C wherein it was saturated by the vapours thereof and then through the catalyst, also at 50°C.

After the oxidation of the catalyst, oxygen was replaced by CO; at the output of the reactor, unreacted $CH_3OH$ and dimethylcarbonate, formed in a cold trap, were condensed. The amount of dimethylcarbonate was quantitative with respect to Cu. No reaction by-product was formed. $CO_2$ was present only as traces.

EXAMPLE 3

2.1 g. of catalyst were charged onto a 6 cc cylindrical reactor, at a pressure of 30 kg/cm$^2$ and a temperature of 50°C. A flow formed by 20 cc/min of $O_2$ and 1.33 cc/h of liquid $CH_3OH$ passed through the reactor and then through a cold trap in order to condense the condensable reaction products and through a baryta water trap to recover $CO_2$.

Methyl alcohol was fed by means of a suitable pump which permits feeding very small amounts of liquids into a reactor at high pressure.

After the oxidation of the catalyst, $O_2$ was replaced by CO. The amount of dimethylcarbonate was practically quantitative with respect to Cu.

More than 10 cycles were carried out at subsequent stages of oxidation and reduction. The amount of dimethylcarbonate was always constant, which meant that the activity of the catalyst had been unchanged; $CO_2$ was present only as traces.

EXAMPLE 4

A flow constituted by 16 cc/min of CO, 5 cc/min of $O_2$, and a flow of 1.33 cc/h of liquid $CH_3OH$ was passed through 2.1 g. loaded in a 6 cc reactor, at a pressure of 30 kg/cm$^2$ and a temperature of 70°C. As described above unreacted $CH_3OH$ and dimethylcarbonate were condensed in a cold trap.

Under such conditions the reaction was carried out for 10 hours. 1.90 g. of dimethylcarbonate were obtained as deduced by comparing, via chromatography analysis, with a standard.

EXAMPLE 5

A flow constituted by 16 cc/min of CO, 5 cc/min of $O_2$ and a flow of 1.33 cc/h of liquid ethyl alcohol were passed through 2.1 g. of catalyst charged in a 6 cc reactor, at a pressure of 30 kg/cm$^2$ and a temperature of 70°C. Unreacted ethyl alcohol and diethylcarbonate were condensed in a cold trap.

Under such conditions the reaction was carried out for 10 hours. 0.95 g. of diethylcarbonate was obtained as shown by chromatography analysis upon comparison with a relevant standard.

EXAMPLE 6

A flow formed by 16 cc/min. of CO and 5 cc/min. of $O_2$ and a flow constituted by 1.33 cc/h of liquid allyl alcohol were passed through the catalyst under the same conditions as those of the preceding example 5 at T=70°C.

0.250 g. of diallylcarbonate was obtained after 10 hours of reaction.

EXAMPLE

A flow formed by 16 cc/min of CO and 5 cc/min of $O_2$ and a flow constituted by a 1.33 cc/h of a methyl alcohol/ethyl alcohol mixture (50%) were passed through 2.1 g. of catalyst at 70°C.

After 10 hours of reaction, 0.80 g. of dimethylcarbonate, 0.38 g. of methylethylcarbonate and 0.15 g. of diethylcarbonate were obtained as shown by chromatography analysis.

What we claim is:

1. A process of carboxylating an alcohol into the corresponding carbonate by reacting the alcohol with oxygen and carbon monoxide in the presence of a catalyst in the disperse phase, wherein said reactants are fed to a reactor charged with a catalyst consisting of a complex of copper chloride and poly-4-vinylpyridine, causing said reactants to flow over said catalyst, and then withdrawing reaction products and unconsumed reactants from the reactor.

2. A process for the carboxylation of an alcohol into the corresponding carbonate as claimed in Claim 1 wherein the reaction is carried out at a temperature in the range of 50° to 80°C.

3. A process for the carboxylation of an alcohol into the corresponding carbonate as claimed in claim 1, wherein the reaction is carried out at a pressure in the range of from one to 200 atmospheres.

4. A process for the carboxylation of an alcohol into the corresponding carbonate as claimed in claim 1, wherein the alcohol is methyl alcohol.

* * * * *